United States Patent
Sakakura et al.

(10) Patent No.: US 6,933,394 B2
(45) Date of Patent: Aug. 23, 2005

(54) CATALYST FOR SYNTHESIZING ALKYLENE CARBONATE

(75) Inventors: Toshiyasu Sakakura, Ibaraki (JP); Hiroyuki Yasuda, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 166 days.

(21) Appl. No.: 10/379,703

(22) Filed: Mar. 6, 2003

(65) Prior Publication Data

US 2004/0024227 A1 Feb. 5, 2004

(30) Foreign Application Priority Data

Mar. 6, 2002 (JP) ........................................ 2002-060422

(51) Int. Cl.$^7$ .......................... C07D 317/12; B01J 31/00
(52) U.S. Cl. ........................ 549/229; 549/230; 502/164
(58) Field of Search ............................. 564/281; 568/16, 568/17; 549/229, 230; 502/164

(56) References Cited

U.S. PATENT DOCUMENTS

| | | |
|---|---|---|
| 4,371,704 A | 2/1983 | McEntire et al. |
| 4,663,467 A | 5/1987 | Kruper, Jr. et al. |
| 4,786,741 A | 11/1988 | Sachs |

FOREIGN PATENT DOCUMENTS

| | | |
|---|---|---|
| GB | 2 113 207 | 8/1983 |

OTHER PUBLICATIONS

European Search Report for 03004908. 4–2117–dated Aug. 6, 2003.
Patent Abstracts of Japan vol. 008, No. 098, May 9, 1984 & JP 59 013766 (Showa Denko K.K.), Jan. 24, 1984.
Patent Abstracts of Japan vol. 005, No. 054, Apr. 15, 1981 & JP 56 008336 (Showa Denko K.K.), Jan. 28, 1981.

*Primary Examiner*—Taofiq Solola
(74) *Attorney, Agent, or Firm*—Sughrue Mion, PLLC

(57) ABSTRACT

The present invention provides an alkylene-carbonate synthesis catalyst comprising a compound insoluble to one phase containing alkylene carbonate produced when the alkylene oxide and carbon dioxide are reacted with the catalyst and soluble to the other phase substantially free of alkylene carbonate. The catalyst allows alkylene carbonate to be produced with high yield and selectivity and be readily collected. The catalyst also facilitates repeated or continuous reaction process in a cost-effective manner. The present invention also provides an apparatus for producing alkylene carbonate using the catalyst.

17 Claims, 3 Drawing Sheets

CATALYST FOR SYNTHESIZING ALKYLENE CARBONATE

FIELD OF THE INVENTION

The present invention relates to a catalyst for synthesizing alkylene carbonate from alkylene oxide and carbon dioxide, and a method and an apparatus for producing alkylene carbonate using the catalyst.

BACKGROUND OF THE INVENTION

Alkylene carbonate is used for various purposes, such as an electrolytic element of lithium secondary batteries, a polar aprotic solvent, a monomer for synthesizing polycarbonate or other polymer, a chemical ingredient for preparing medicines or agricultural chemicals, and an alkylating agent.

Heretofore, alkylene carbonate has been produced by reacting alkylene oxide with carbon dioxide under normal or higher pressure and in the presence of a homogeneous catalyst such as alkali metal halide, ammonium salt or phosphonium salt.

In the method using the homogeneous catalyst, the catalyst is undesirably dissolved in a phase containing a reaction product or alkylene carbonate. Thus, it is required to separate the catalyst from the product through a process such as distillation after completion of the reaction, resulting in complicated production processes, and decomposition of the catalyst or formation of by-products during the separation process.

In order to facilitate the separation of the catalyst, there have been proposed various solid catalysts, such as an ion exchange resin containing a quaternary ammonium group or a quaternary phosphonium group as an exchange group (Japanese Patent Publication Nos. 3-120270, 7-206846, 7-206848, 9-235252 etc.), a heteropoly acid or salt thereof (Japanese Patent Publication No. 7-206847), MgO (T. Yano et al., Chem. Commun., 1129 (1997)), and a complex oxide obtained by burning a basic layered compound (Japanese Patent Publication No. 11-226413; K. Yamaguchi et al., J. Am. Chem. Soc., 121, 4526 (1999)).

However, these solid catalysts have insufficient activity because their active site is limited to a solid surface, due to its insolubility to a reaction product and reaction components, such as carbon dioxide and alkylene oxide, and, in addition, they are subject to interference from dissolved reaction components. While the reaction temperature can be increased to improve activity, it may deteriorate catalyst selectivity. In particular, the ion exchange resin catalysts have a limited reaction temperature due to poor heat-resistance. Most solid catalysts are essentially required to contain an aprotic polar solvent as an additive for assuring activity and selectivity. In addition, most solid catalysts suffer from degradation due to elution of catalyst components into the reaction product or alkylene carbonate.

SUMMARY OF THE INVENTION

In view of the above problems in the production of alkylene carbonate, it is therefore an object of the present invention to provide a catalyst capable of synthesizing alkylene carbonate in high yield and with high selectivity while facilitating the collection of the product and the separation of the catalyst after reaction process and to allow the reaction process to be performed repeatedly or continuously without any difficulty.

It is another object of the present invention to provide a method and an apparatus for producing alkylene carbonate using the catalyst, with advantages in commercial and economical terms.

In order to achieve the above object, the inventors prepared a catalyst comprising a compound insoluble to a phase containing alkylene carbonate that is produced using the catalyst and soluble to a phase substantially free of alkylene carbonate. The inventors found the following facts. First, the catalyst provides enhanced reaction efficiency. Second, during reaction using the catalyst, the resulting mixture is gradually separated into one phase substantially free of alkylene carbonate [high-density carbon dioxide phase (upper layer)] and a second phase containing alkylene carbonate [alkylene carbonate phase (lower layer)]. The high-density carbon dioxide phase is substantially free of alkylene carbonate, that is, it preferably contains less than about 5%, more preferably less than about 1% of alkylene carbonate. It would be apparent to one of ordinary skill in the art that sufficient alkylene carbonate could be found in the high-density carbon dioxide phase for the reaction to be repeated. Thus, the product can be readily collected while maintaining the density of the carbon dioxide phase at a high value. In addition, the catalyst can also be readily separated from the product because the catalyst is soluble in the high-density carbon dioxide phase. Thirdly, the catalyst facilitates repeated or continuous reaction. Based on the above knowledge, the inventors have finally accomplished the present invention.

According to the first aspect of the present invention, there is provided a catalyst for synthesizing alkylene carbonate from alkylene oxide and carbon dioxide. The catalyst is comprised of a compound insoluble to a first phase containing alkylene carbonate that is produced using the catalyst and soluble in a second phase substantially free of alkylene carbonate.

In the catalyst set forth in the first aspect of the present invention, the compound preferably is a quaternary phosphonium salt or quaternary ammonium salt having at least one group selected from an alkyl group, an arylalkyl group, an alkenyl group and an aryl group. In this case, one or more hydrogen atoms on at least one carbon atom of the group are substituted with fluorine atom.

According to a second aspect of the present invention, there is provided a method for producing alkylene carbonate by reacting alkylene oxide with carbon dioxide in the presence of the catalyst set forth in the first aspect of the present invention.

The method set forth in the second aspect of the present invention preferably comprises the following steps: (a) reacting an alkylene oxide with carbon dioxide in the presence of the catalyst to form a mixture that includes a first phase containing alkylene carbonate and a second phase containing at least a part of the catalyst dissolved therein substantially free of alkylene carbonate; (b) collecting the alkylene carbonate from the first phase while maintaining the second phase; (c) adding a given amount of alkylene oxide and carbon dioxide to the second phase; and (d) repeating the steps (b) and (c).

Alternatively, the method preferably comprises the following steps: (a) reacting alkylene oxide with carbon dioxide in the presence of the catalyst to form a mixture that includes a first phase containing alkylene carbonate and a second phase containing at least a part of the catalyst dissolved therein and substantially free of alkylene carbonate; and (b) continuously collecting alkylene carbonate from the first phase while maintaining the second phase, and continuously adding a given amount of alkylene oxide and carbon dioxide to the second phase.

Alternatively, the method preferably comprises the following steps: (a) reacting alkylene oxide with carbon dioxide in the presence of the catalyst in a reactor to form a mixture that includes a first phase containing alkylene carbonate and a second phase containing at least a part of the catalyst dissolved therein and substantially free of alkylene carbonate; (b) transferring the mixture to a collector; (c) collecting alkylene carbonate from the first phase while maintaining the second phase in the collection area; (d) returning the second phase to the reaction area, and adding a given amount of alkylene oxide and carbon dioxide to the second phase to allow the step (a) to be performed; and (e) repeating the steps (a) to (c).

According to a third aspect of the present invention, there is provided an apparatus for producing alkylene carbonate. The apparatus comprises a means for reacting alkylene oxide with carbon dioxide in the presence of a catalyst to form a mixture that includes a first phase containing alkylene carbonate and a second phase containing at least a part of the catalyst dissolved therein and substantially free of alkylene carbonate. The catalyst includes a compound insoluble to the first phase and soluble in the second phase. The apparatus further includes (b) means for collecting alkylene carbonate from the first phase while maintaining the second phase, (c) means for adding a given amount of alkylene oxide and carbon dioxide to the second phase, and (d) means for separately controlling said collecting means and said adding means.

According to a fourth aspect of the present invention, there is provided an apparatus for producing alkylene carbonate. The apparatus comprises (a) means for reacting alkylene oxide with carbon dioxide in the presence of a catalyst to form a mixture including a first phase containing alkylene carbonate and a second phase containing at least a part of the catalyst dissolved therein and substantially free of alkylene carbonate. The catalyst includes a compound insoluble to the first phase and soluble in the second phase. The apparatus further includes (b)means for continuously collecting alkylene carbonate from the first phase while maintaining the second phase, and continuously adding a given amount of alkylene oxide and carbon dioxide to the second phase.

According to a fifth aspect of the present invention, there is provided an apparatus for producing alkylene carbonate. The apparatus comprises (a) means for reacting alkylene oxide with carbon dioxide under the presence of a catalyst in a reactor to form a reacted mixture including a first phase containing alkylene carbonate and a second phase containing at least a part of the catalyst dissolved therein and substantially free of alkylene carbonate. The catalyst included a compound insoluble to the first phase and soluble to the second phase. The apparatus further includes (b) means for transferring the reacted mixture to a collection area, (b) means for collecting alkylene carbonate from the first phase while maintaining the second phase in the collection area, (c) means for returning the second phase to the reaction area, and adding a given amount of alkylene oxide and carbon dioxide to the second phase.

The alkylene-carbonate synthesis catalyst of the present invention allows alkylene carbonate to be produced from alkylene oxide and carbon dioxide with enhanced efficiency and selectivity. The obtained alkylene carbonate can be used for an electrolytic element of lithium secondary batteries, polar aprotic solvent, monomer for synthesizing polycarbonate or other polymer, chemical ingredient for preparing medicines or agricultural chemicals, alkylating agent or the like.

Further, the method and apparatus of the present invention can facilitate the collection of the product and the separation of the catalyst after reaction, and repeated or continuous reaction process to achieve significant energy saving. The method and apparatus of the present invention provides significant advantages in environmental, commercial and economical terms.

DESCRIPTION OF THE PREFERRED EMBODIMENT

Figure 1:
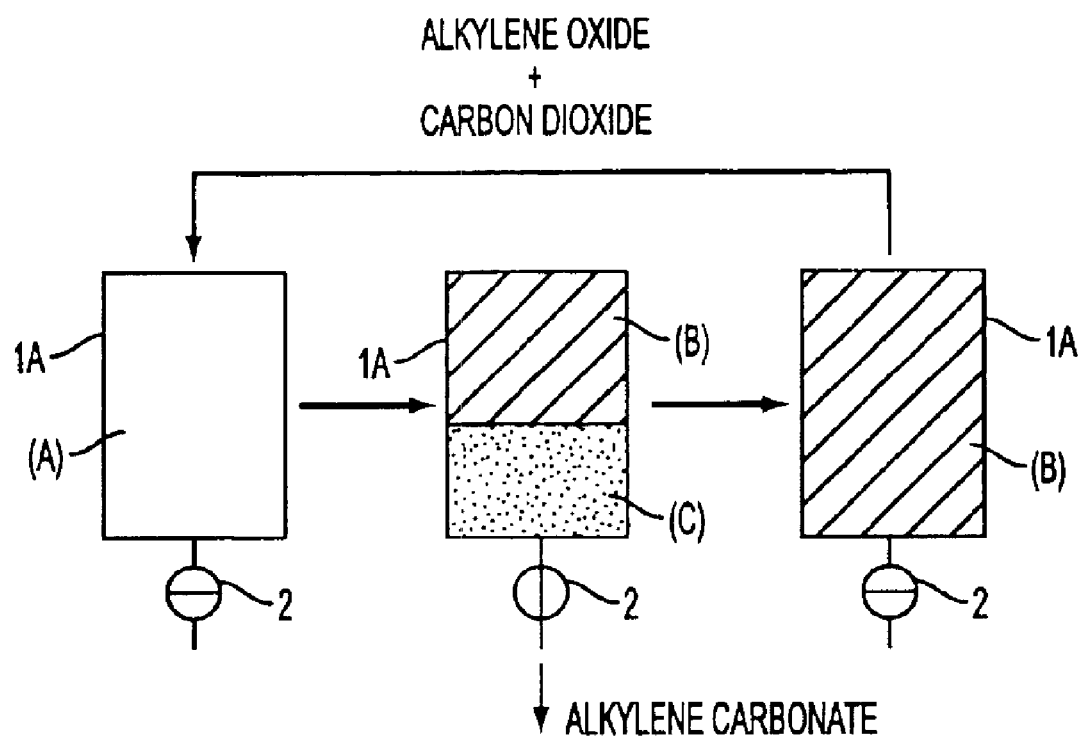
FIG. 1 illustrates an alkylene-carbonate production process according to a first embodiment of the present invention.
Figure 1:
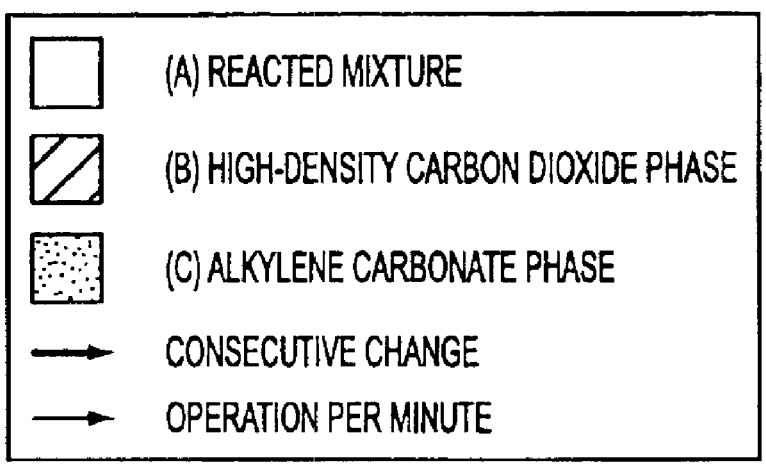

In the present invention, the synthesis reaction between alkylene oxide and carbon dioxide produces alkylene carbonate and is represented by the following general formula (1).

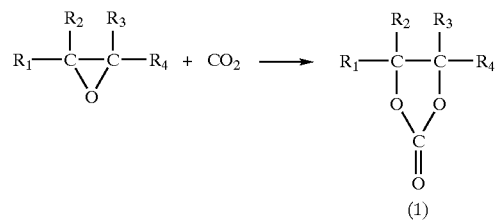

(1)

In the general formula (1), each of $R_1$, $R_2$, $R_3$ and $R_4$ represents either an alkyl group, aryl group, alkenyl group, cycloalkyl, or arylalkyl group the group including 15 or less carbon atoms, each carbon atom having one or more hydrogen atoms or substituents, or having no substituent. $R_1$, $R_2$, $R_3$ and $R_4$ may be the same or different. The term "substituent" herein means a halogen atom, a dialkyl group, an amino group, a nitro group, a carbonyl group, a carboxyl group, an alkoxy group, an acetoxy group, a hydroxyl group, a mercapto group, or a sulfonic group.

Alkylene oxide to be used in the present invention has the following general formula (2).

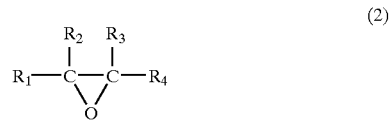

(2)

In the general formula (2), $R_1$, $R_2$, $R_3$ and $R_4$ are the same as those in the general formula (1). While the alkylene oxide may be ethylene oxide, propylene oxide, butylene oxide, vinylethylene oxide, cyclohexene oxide and styrene oxide, the present invention is not limited to these alkylene oxides. Any suitable compound having a structural formula including at least one 3-member ring consisting of two carbon atoms and one oxygen atom, i.e. epoxy compounds, may be used.

Alkylene carbonate to be produced according to the present invention is a compound as shown in the following general formula (3).

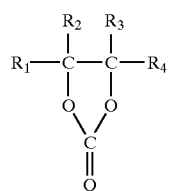
(3)

In the general formula (3), $R_1$, $R_2$, $R_3$ and $R_4$ are the same as those in the general formula (1). Specifically, the alkylene carbonate may be ethylene carbonate, propylene carbonate, butylene carbonate, vinylethylene carbonate, cyclohexene carbonate, and styrene oxide.

In view of esterification reaction activity and separation from a reaction product, a catalyst to be used in the present invention may include any compound insoluble to a first phase containing alkylene carbonate produced when the alkylene oxide and carbon dioxide are reacted with the catalyst and soluble to a second phase substantially free of alkylene carbonate.

Preferably, the catalyst may be a quaternary phosphonium salt or a quaternary ammonium salt represented by the following general formula (4).

(4)

In the general formula, Rf represents a group selected from the group consisting of alkyl, arylalkyl, alkenyl and aryl groups, wherein one or more hydrogen atoms on at least one carbon atom of the group are substituted with a fluorine atom. R represents any group selected from the group consisting of alkyl, arylalkyl, alkenyl and aryl groups. M represents phosphorous or nitrogen atom. X represents chlorine, bromine, or iodine atom, and m represents any integer of 1 to 4. When the compound has two or more Rf's or R's linked to M, Rfs or R's may be the same or different.

The alkyl group represented by Rf may have a chain or circular structure, and may have a normal or branched chain structure. The Rf group contains one or more substituted fluorine atoms on one or more carbon atoms. In the alkyl group, the number of carbon atoms is preferably in the range of 4 to 10. The alkyl group may be, for example, perfluorobutyl, perfluorohexyl, 2-(perfluorohexyl) ethyl, perfluorooctyl, 2-(perfluorooctyl) ethyl and perfluorodecyl.

The arylalkyl group represented by Rf, in which one or more hydrogen atoms on at least one carbon atom are substituted with a fluorine atom, preferably has carbon atoms in the range of 7 to 10. The arylalkyl group may be, for example perfluorobenzyl, perfluorophenethyl, perfluoronaphtyl methyl and perfluoro-2-naphtyl ethyl.

The alkenyl group represented by Rf, in which one or more hydrogen atoms on at least one carbon atom are substituted with a fluorine atom, preferably has carbon atoms in the range of 2 to 10. The alkenyl group may be, for example, perfluorovinyl, perfluoroallyl, perfluorocyclopentadienyl, perfluoro-pentamethylcyclopentadienyl, and perfluoroindenyl.

The aryl group represented by Rf, in which one or more hydrogen atoms on at least one carbon atom are substituted with a fluorine atom, preferably has carbon atoms in the range of 6 to 14. The aryl group may be, for example, perfluorophenyl, perfluorotolyl, perfluoroanisyl, perfluoronaphthyl, and p-trifluoromethyl phenyl.

The alkyl group represented by R may have a chain or circular structure and may have a normal or branched chain structure. The number of carbon atoms is preferably in the range of 1 to 4. The alkyl group may be, for example, methyl, ethyl, n-propyl, isopropyl, and n-butyl. The arylalkyl group represented by R preferably has 7 to 10 carbon atoms. The arylalkyl group may be, for example, benzyl, phenethyl, naphtyl methyl and 2-naphtyl ethyl. The alkenyl group represented by R preferably has 2 to 10 carbon atoms. The alkenyl group may have a chain or circular structure. The alkenyl group may be, for example, vinyl, allyl, cyclopentadienyl, pentamethylcyclopentadienyl and indenyl. The aryl group represented by R preferably has 6 to 14 carbon atoms. The aryl group may be, for example, phenyl, tolyl, anisyl and naphthyl.

While the above catalysts have been shown as representative examples, the catalyst of the present invention is not limited to the above catalysts but includes any other suitable compound having the desired catalytic esterifcation activity and the desired selective solubility, i.e., both the insolubility to a first phase containing alkylene carbonate produced when the alkylene oxide and carbon dioxide are reacted with the catalyst and the solubility to a phase substantially free of alkylene carbonate may be used.

While the catalyst of the present invention need not contain any particular auxiliary additive therein, it may contain some additive to provide enhanced selectivity to alkylene carbonate and increased yield of alkylene carbonate.

The additive may include a so-called aprotic polar solvent, such as dimethylformamide, N-methylpyrrolidone, acetonitryl, dimethylsulfoxide or dimethylacetamide. The yield and selectivity of alkylene carbonate can also be improved by adding pre-produced alkylene carbonate into the reaction system in advance. The alkylene carbonate serving as an additive may include ethylene carbonate, propylene carbonate, butylene carbonate, vinylethylene carbonate, cyclohexene carbonate and styrene carbonate.

The alkylene-carbonate production method of the present invention will now be described in conjunction with specific embodiments.

In the alkylene-carbonate production method of the present invention, alkylene carbonate is produced by reacting alkylene oxide with carbon dioxide in the presence of a catalyst comprising a compound insoluble to a first phase containing alkylene carbonate produced when the alkylene oxide and carbon dioxide are reacted with the catalyst and soluble to a second phase substantially free of alkylene carbonate.

During the esterification reaction between alkylene oxide and carbon dioxide, the reacted mixture is formed as a homogeneous phase in the initial stage of the reaction process, and then gradually separated into at least two phases: a first phase containing alkylene carbonate (lower layer, hereinafter occasionally referred to as "alkylene carbonate phase") and a second phase containing at least a part of the catalyst dissolved therein and substantially free of alkylene carbonate (upper layer, hereinafter occasionally referred to as "high-density carbon dioxide phase").

The high-density carbon dioxide phase primarily includes high-density carbon dioxide, unreacted alkylene oxide, and at least a part of the dissolved catalyst.

The alkylene carbonate phase is primarily comprised of alkylene carbonate as produced by the reaction. Relatively small amounts of the catalyst will be contained in the alkylene carbonate phase because it should be dissolved in the upper layer, i.e. the high-density carbon dioxide phase according to its selective solubility.

The method of the present invention utilizes the above separation so alkylene carbonate can be produced in high yield and selectivity through a batch or continuous process.

With reference to the drawings, representative embodiments of the process will be described.

FIG. 1 shows a flow chart of the batch process. The reference code 1A indicates a batch vessel type reactor, reference code 2 indicates a collecting device, reference code (A) indicating a reacted mixture containing a catalyst dissolved therein, reference code (B) indicating a second phase containing the catalyst dissolved therein and substantially free of alkylene carbonate (high-density carbon dioxide phase), and reference code (C) indicating a first phase containing alkylene carbonate (alkylene carbonate phase).

During reaction process, the reacted mixture (A) in the reactor 1A is gradually separated into the high-density carbon dioxide phase (B) and the alkylene carbonate phase (C). The produced alkylene carbonate is extracted and collected from the lower layer or the alkylene carbonate phase (C) through the collecting device 2 (for example, a product-discharge valve attached to the bottom of the reactor), while maintaining the high value of the density of the upper layer or the carbon dioxide phase (B), for example, in the reactor 1A. Then, a given amount of alkylene oxide and carbon dioxide raw material (is added to the upper layer or the high-density carbon dioxide (B). After the pressure is readjusted to a predetermined pressure, the initial stage reaction is reperformed in the reactor 1A for a given period. The above process can be sequentially repeated to produce alkylene carbonate high in yield and purity.

Figure 2:
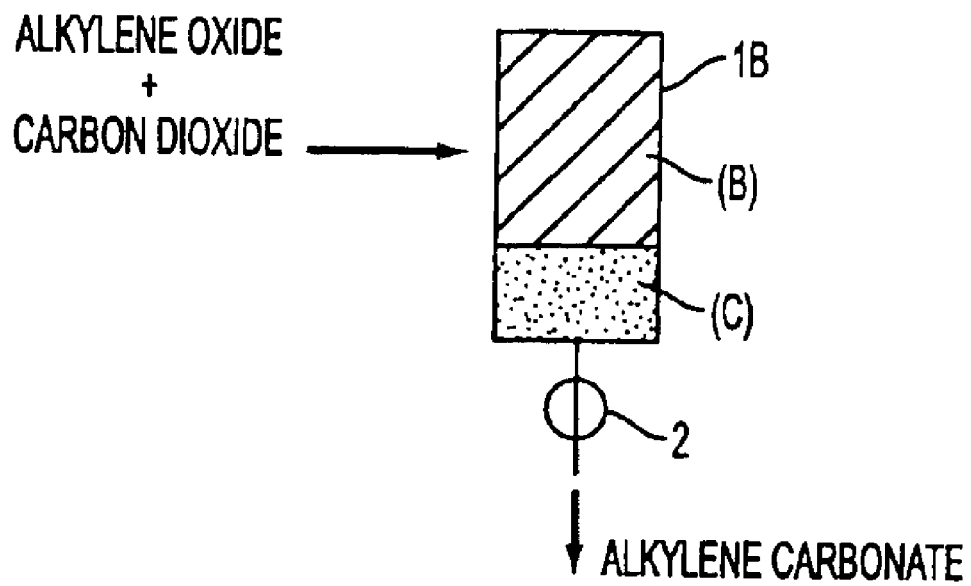
FIG. 2 illustrates an alkylene-carbonate production process according to a second embodiment of the present invention.
Figure 2:
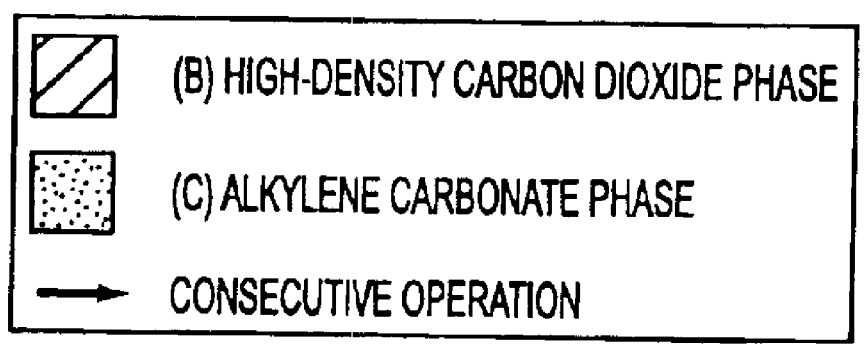

FIG. 2 shows a flow chart of the continuous process. In this process, a continuous-flow vessel type reactor 1B is typically used. As with the batch process, the mixture is gradually separated into the high-density carbon dioxide phase (B) and the alkylene carbonate phase (C). This present process effectively utilizes this phenomenon. That is, additional alkylene oxide and carbon dioxide are continuously supplied by an amount consumed through the reaction to the high-density carbon dioxide phase (B) containing the catalyst and the unreacted alkylene oxide in the reactor 1B, and the produced alkylene carbonate is continuously collected through the collecting device 2. This method allows alkylene carbonate to be continuously produced in high yield and purity.

Figure 3:
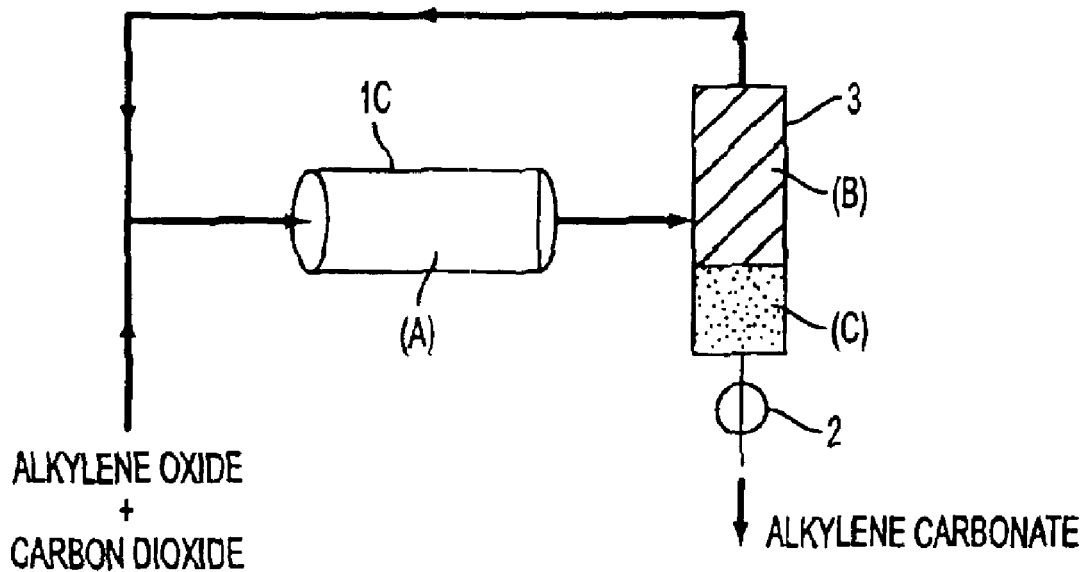
FIG. 3 illustrates an alkylene-carbonate production process according to a third embodiment of the present invention.
Figure 3:
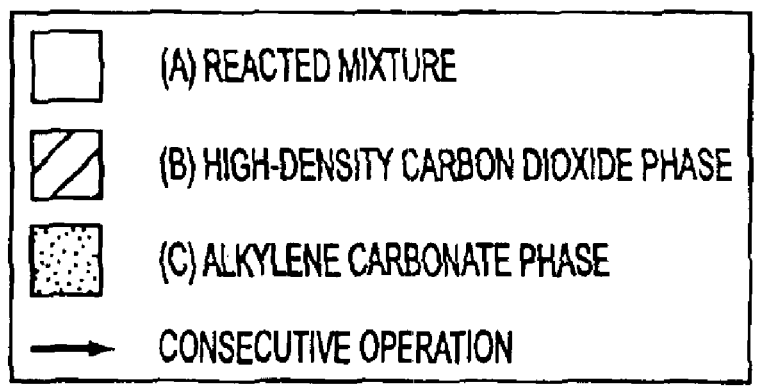

FIG. 3 shows another flow chart of the continuous process. This continuous process typically employs a continuous-flow tube type reactor 1C and a separator 3 independent of the reactor 1C. In this process, the mixture (A) obtained in the reactor 1C is transferred to the independent separator 3. The transferred mixture (A) is separated into the high-density carbon dioxide phase (B) and the alkylene carbonate phase (C). Then, the produced alkylene carbonate is collected from the alkylene carbonate phase, which contains no catalyst through the collecting device 2 while maintaining the upper layer or the high-density carbon dioxide phase (B). Simultaneously, the high-density carbon dioxide phase (B) containing the dissolved catalyst is circulated to the reactor 1C, and then a given amount of alkylene oxide and carbon dioxide are added to the reactor 1C. This method also allows alkylene carbonate to be continuously produced in high yield and purity.

Thus, the method of the present invention can eliminate the need for separating the catalyst and the reaction product from the mixture, simplify the production process, and facilitate the collection of the product and the separation of the catalyst after the reaction process. In addition, the method of the present invention allows the reaction process to be performed repeatedly or continuously without any difficulty.

The present invention utilizes the catalyst's selective solubility in the high-density carbon dioxide phase. Thus, as a practical matter, it is desirable to increase the solubility of the catalyst to the high-density carbon dioxide. For this purpose, liquefied carbon dioxide may be pressure-injected into the mixture through a liquid feed pump or the like to maintain the density of the carbon dioxide in the reaction system to at least 0.1 $g/cm^3$ or more.

The reaction temperature may be set, but not limited to, generally in the range of 25° C. to 300° C., preferably 40° C. to 200° C. to allow the density of the carbon dioxide to be maintained at a high value.

The reaction pressure may also be set at any suitable pressure that allows the density of the carbon dioxide to remain at a high value. Specifically, the reaction pressure may be set in the range from 1 to 100 Map, preferably 5 to 30 Map, depending on the production cost of a pressure-resistant equipment for the reaction process.

The amount of the catalyst and the reaction time are varied according to the type of the reactor, the kind of alkylene oxide as a raw material, reaction temperature, reaction pressure, desired productivity and other factors. When a batch vessel type reactor is used, the moll ratio of the catalyst to the alkylene oxide preferably is 0.1:1 to 0.000001:1, preferably 0.01:1 to 0.0001:1, and the reaction time is preferably 0.1 to 30 hours.

The alkylene-carbonate production apparatus of the present invention will be described below.

A reactor of the apparatus may be any suitable conventional reactor, such as a batch vessel type reactor (1A in FIG. 1), a continuous-flow vessel type reactor (1B in FIG. 2), or a continuous-flow tube type reactor (1C in FIG. 3).

The apparatus of the present invention can extract the produced alkylene carbonate from the alkylene carbonate phase containing no catalyst because the mixture is gradually separated into the high-density carbon dioxide phase (upper layer) and the alkylene carbonate phase (lower layer) during the reaction process. Thus, it is desired to provide a separator capable of allowing the alkylene carbonate phase to be collected while maintaining the density of the upper layer or the carbon dioxide phase at a high value when both phases coexists.

Specifically, the separator is preferably provided with a collecting device capable of collecting only alkylene carbonate by opening a valve at the bottom or lower region in the separator as shown in FIGS. 1 and 2 while maintaining the high-density value of the carbon dioxide phase located in the upper region in the separator.

The reactor may be commonly used as a separator as shown in FIGS. 1 and 2, or a separator may be provided independently of the reactor. The latter may be a batch or continuous-flow type reactor operable to circulate the mixture containing the high-density carbon dioxide, the unreacted alkylene oxide and the catalyst, between the tube type reactor 1C and the separator 3 as shown in FIG. 3.

The above collection process may be conducted under the same temperature and pressure as those in the reaction process. Alternatively, the conditions in the collection process may be set at a different temperature and pressure from those in the reaction process to provide enhanced collection efficiency. It is desirable to regulate the temperature and pressure for the collection process to maintain the density of the carbon dioxide at a high value. Specifically, the temperature in the collection process is preferably 40° C. to 200° C., the pressure in the collection process is preferably 5 to 100 MPa.

The operation of the apparatus, for example using a batch vessel type reactor, will be described below. A catalyst that it selectively soluble to the alkylene oxide and the high-density carbon dioxide is added to an autoclave having a stirrer and a product-discharge valve, and then the autoclave is filled with liquefied carbon dioxide from a carbon dioxide container, and sealed, wherein the pressure is equal to that of the carbon dioxide container. The mixture in the autoclave is heated up to a given temperature while stirring it, and the autoclave is supplied with carbon dioxide in order to adjust the internal pressure thereof. Then, the mixture is reacted for a given time. In the initial stage of the reaction process, the mixture is a homogeneous phase, and gradually separated into two phases. When the reaction process is completed, the mixture is separated into the high-density carbon dioxide phase (upper layer) and the alkylene carbonate phase (lower layer). The produced alkylene carbonate can be easily collected by opening the product-discharge valve while maintaining the high density value of the upper layer in the reactor.

The alkylene-carbonate production apparatus of the present invention can readily perform repeated or continuous reaction processes as described below.

After performing the above reaction process using the batch vessel type reactor 1A as shown in FIG. 1, and collecting the alkylene carbonate from the alkylene carbonate phase (C) through the collecting device 2, a given amount of alkylene oxide and carbon dioxide as raw materials are added to the high-density carbon dioxide phase (B) containing the catalyst dissolved therein, and the pressure is readjusted to a given pressure. Then, the same reaction process as the last process can be repeated in order to conduct the continuous reaction process.

The continuous reaction process can also be conducted using a continuous-flow vessel type reactor as shown in FIG. 2, 1B. Specifically, additional alkylene oxide and carbon dioxide are continuously supplied to the high-density carbon dioxide phase (B) containing the catalyst and the unreacted alkylene oxide in the reactor 1B, and the produced alkylene carbonate is continuously collected from the alkylene carbonate phase (C) through the collecting device 2. This method allows alkylene carbonate to be continuously produced in high yield and purity.

Alternatively, the continuous reaction process can be conducted using a continuous-flow tube type reactor and a separator independent of the reactor as shown in FIG. 3. Specifically, the catalyst and the alkylene oxide and carbon dioxide of raw materials are supplied to the tube type reactor 1C, and reacted with each other. Then, the mixture (A) is transferred to the independent separator 3. The produced alkylene carbonate is collected from the alkylene carbonate phase (C) containing no catalyst through the collecting device 2 while maintaining the upper layer or the high-density carbon dioxide phase (B). Simultaneously, the high-density carbon dioxide phase (B) containing the dissolved catalyst is circulated to the reactor 1C, and then a given amount of alkylene oxide and carbon dioxide are added to the reactor 1C. As above, this apparatus can continuously produce alkylene carbonate in high yield and purity.

While the present invention will be described in more detail in conjunction with to the following examples, it should be understood that they are intended to limit the present invention.

EXAMPLE 1

Synthesis of tri(2-(perfluorohexyl)ethyl) methylphoshonium iodide (($C_6F_{13}C_2H_4$)$_3CH_3PI$)

Ether (85 ml) and (2-(perfluorohexyl)ethyl iodide) (12.4 ml) were put in activated metal magnesium (1.44 g), and the mixture was circulated for 2 hours to obtain 2-(perfluorohexyl)ethyl magnesium iodide. Phosphine trichloride (1.4 ml) dissolved in ether (75ml) was added to the product, and the mixture was stirred for one night. Then, the mixture was hydrolyzed by ammonium chloride solution (20 ml) in order to separate the oil phase. The oil phase was dried by magnesium sulfate, and the solvent is removed from the dried phase under a reduced pressure to obtain crude tri(2-(perfluorohexyl)ethylphosphin(($C_6F_{13}C_2H_4$)$_3P$)). The crude product was then dissolved in ether (10 ml). The solution is purified through an alumina column, and the solvent is removed under reduced pressure to obtain a purified product of (($C_6F_{13}C_2H_4$)$_3P$)). Then, acetone (20 ml) and methyl iodide (2.27 g) were added to (($C_6F_{13}C_2H_4$)$_3P$), and the mixture was circulated for 3 days. Then, the product was rinsed with ether several times, and dried to synthesize (($C_6F_{13}C_2H_4$)$_3CH_3PI$). The structure of (($C_6F_{13}C_2H_4$)$_3CH_3PI$) was confirmed through NMR (1H, 13C, 31P) and elemental analysis.

Synthesis of Alkylene Carbonate

Under an Ar atmosphere, a solution of propylene oxide (4 ml) and (($C_6F_{13}C_2H_4$)$_3CH_3PI$)(1 mol %), as the catalyst, were put in a 20 ml autoclave having a stirrer and a valve for extracting the lower layer. Then, the autoclave was filled with liquefied carbon dioxide from a carbon dioxide container, and sealed. The mixture in the autoclave was heated up to 100° C. while stirring it, and the autoclave was additionally supplied with carbon dioxide to adjust the inner pressure to 14 MPa. The mixture was left for 24 hours. Then, the product solution in the lower layer was collected by opening the product-discharge valve at 100° C. Through gas chromatography analysis, it was verified that the obtained product was propylene carbonate yielding 93%. The inside pressure was reduced down to 12 MPa due to the increase of internal volume as a result of the collection of the lower layer. Propylene oxide (4 ml) and carbon dioxide were additionally supplied into the mixture of the high-density carbon dioxide and the catalyst in the reactor, and reacted at 100° C. under 14 MPa for 24 hours. Then, propylene carbonate with a yield of 93% was collected while maintaining the catalyst in the upper layer.

EXAMPLE 2

The reaction process was performed in the same manner as that in Example 1 except that the catalyst was changed to tri(2-(perfluorooctyl)ethyl)methyl phosphonium iodide ((C8F17C2H4) 3CH3OI) (($C_8F_{17}C_2H_4$)$_3CH_3OI$). As a result, propylene carbonate with a yield of 92% was obtained.

In Example 2, tri(2-(perfluorooctyl)ethyl)methyl phosphonium iodide (($C_8F_{17}C_2H_4$)$_3CH_3PI$) was synthesized by using 2-(perfluorohexyl)ethyl iodide as a substitute for 2-(perfluorooctyl)ethyl iodide.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of this invention.

What is claimed is:

1. A catalyst for synthesizing alkylene carbonate from alkylene oxide and carbon dioxide comprising a quaternary phosphonium salt or a quaternary ammonium salt represented by the following general formula (4), $$Rf_mR_{(4-m)}MX \qquad (4)$$

wherein Rf represents a group selected from the group consisting of alkyl, arylalkyl, alkenyl and aryl groups, and one or more hydrogen atoms on at least one carbon atom of the group is substituted with a fluorine atom, R represents any group selected from the group consisting of alkyl, arylalkyl, alkenyl and aryl groups, and when two or more Rf's or R's are bonded to M, the Rf's or R's may be the same or different, M represents phosphorous or nitrogen atom, X represents chlorine, bromine, or iodine atom, and m represents any integer of 1 to 4.

2. The catalyst according to claim 1, wherein at least one $R_f$ is an alkyl group having 4 to 10 carbon atoms.

3. The catalyst according to claim 2, wherein the alkyl group is selected from the group consisting of perfluorobutyl, perfluorohexyl, 2-(perfluorohexyl)ethyl, perfluorooctyl, 2-(perfluorooctyl)ethyl and perfluorodecyl groups.

4. The catalyst according to claim 1, wherein at least one Rf is an arylalkyl group having 7 to 10 carbon atoms.

5. The catalyst according to claim 4, wherein the arylalkyl group is selected from the group consisting of perfluorobenzyl, perfluorophenethyl, perfluoronaphtyl methyl and perfluoro-2-naphtyl ethyl groups.

6. The catalyst according to claim 1, wherein at least one $R_f$ is an alkenyl group having 2 to 10 carbon atoms.

7. The catalyst according to claim 6, wherein the alkenyl group is selected from the group consisting of perfluorovinyl, perfluoroallyl, perfluorocyclopentadienyl, perfluoro-penta-methylcyclopentadienyl, and perfluoroindenyl groups.

8. The catalyst according to claim 1, wherein at least one $R_f$ is an aryl group having 6 to 14 carbon atoms.

9. The catalyst according to claim 8, wherein the aryl group is selected from the group consisting of perfluorophenyl, perfluorotolyl, perfluoroanisyl, perfluoronaphthyl, and p-trifluoromethyl phenyl.

10. The catalyst according to claim 1, wherein at least one R is an alkyl group having 1 to 4 carbon atoms.

11. The catalyst according to claim 10, wherein the alkyl group is selected from the group consisting of methyl, ethyl, n-propyl, isopropyl, and n-butyl groups.

12. The catalyst according to claim 1, wherein at least one R is an arylalkyl group having 7 to 10 carbon atoms.

13. The catalyst according to claim 12, wherein the arylalkyl group is selected from the group consisting of benzyl, phenethyl, naphtyl methyl and 2-naphtyl ethyl groups.

14. The catalyst according to claim 1, wherein at least one R is an alkenyl group having 2 to 10 carbon atoms.

15. The catalyst according to claim 14, wherein the alkenyl group is selected from the group consisting of vinyl, allyl, cyclopentadienyl, pentamethylcyclopentadienyl, and indenyl groups.

16. The catalyst according to claim 1, wherein at least one R is an aryl group having 6 to 14 carbon atoms.

17. The catalyst according to claim 16, wherein the aryl group is selected from the group consisting of phenyl, tolyl, anisyl, and naphthyl.

\* \* \* \* \*